United States Patent [19]

Hattori et al.

[11] 4,145,539

[45] Mar. 20, 1979

[54] PROCESS FOR ISOLATION AND PURIFICATION OF CEPHALOSPORIN COMPOUND

[75] Inventors: Kiyoshi Hattori, Takarazuka; Takashi Mitamura, Ibaragi, both of Japan

[73] Assignee: Fujisawa Pharmaceutical Co., Ltd., Osaka, Japan

[21] Appl. No.: 788,012

[22] Filed: Apr. 15, 1977

[30] Foreign Application Priority Data

Apr. 20, 1976 [JP] Japan .................................. 51/45131

[51] Int. Cl.² ........................................... C07D 501/12
[52] U.S. Cl. .................................................. 544/20
[58] Field of Search ....................... 260/243 C; 544/20

[56] References Cited

U.S. PATENT DOCUMENTS

| | | | |
|---|---|---|---|
| 3,709,880 | 1/1973 | Goegelman et al. | 260/243 C |
| 3,725,400 | 4/1973 | Voser | 260/243 C |
| 3,979,383 | 9/1976 | Wild | 544/20 |
| 4,028,355 | 6/1977 | Blackburn | 544/20 |

*Primary Examiner*—Nicholas S. Rizzo
*Attorney, Agent, or Firm*—Dayton R. Stemple, Jr.

[57] ABSTRACT

A process for the isolation and purification of cephalosporin from a solution containing impurities which includes treating the solution with macroporous non-ionic adsorption resin to adsorb the cephalosporin thereto and then eluting the cephalosporin from the resin with an aqueous solution of anionic surface active agent.

9 Claims, No Drawings

PROCESS FOR ISOLATION AND PURIFICATION OF CEPHALOSPORIN COMPOUND

This invention relates to a process for the isolation and purification of cephalosporin compound, and more particalarly to a process for the isolation and purification of cephalosporin compound from a solution containing it in admixture with impurities, which comprises treating the solution with macroporous non-ionic adsorption resin and then eluting the cephalosporin compound from the resin with an aqueous solution of anionic surface active agent.

The following processes have been known for the isolation of a cephalosporin compound from a solution containing it in admixture with impurities.

(a) A process for the isolation of cephalosporin C from a solution containing it, which comprises treating the solution with macroporous, non-ionic styrene-divinylbenzene copolymer adsorption resin and then eluting cephalosporin C from the resin with a mixture of water and a water-miscible organic solvent (U.S. Pat. No. 3,725,400).

(b) A process for the purification of cephalosporin compound having a free carboxy group, which comprises treating an aqueous solution containing it with macroporous, non-ionic adsorption resin consisting of styrene-divinylbenzene copolymer or acrylic acid ester polymer and then eluting the cephalosporin compound from the resin with an aqueous solution of a pH value of 3–8.5 (German Offenlegungsschrift No. 2,502,097).

(c) A process for the isolation and purification of cephalosporin C, which comprises treating a solution containing it with macroporous, non-ionic adsorption resin and then eluting cephalosporin C from the resin with an eluent such as water, an aqueous solution of alkali metal hydroxide or alkali metal salt (Japanese patent laid open No. 32,791/1976).

However, these processes are not satisfactory for the isolation and purification of the cephalosporin compounds, especially in respect of purity of the isolated cephalosporin compound, which is due to the fact that considerable amounts of the impurities are eluted from the resin together with the cephalosporin compound.

The inventors of this invention have conducted extensive studies for improving the prior methods as mentioned above, and finally succeeded in recovering selectively the adsorbed cephalosporin compound from the resin in high purity as well as high yield by using an aqueous solution of an anionic surface active agent as a specified eluent.

Accordingly, an object of this invention is to provide a process for the isolation and purification of cephalosporin compound from a solution containing it in admixture with impurities in high purity and high yield.

Further object of this invention is to provide a process for the isolation and purification of cephalosporin compounds which comprises the usage of macroporous, non-ionic adsorption resin as an adsorbent and the usage of an aqueous solution of an anionic surface active agent as an eluent.

As the first step of the process of this invention, there is effected the treatment of a solution containing a cephalosporin compound in admixture with impurities with macroporous, nonionic adsorption resin.

The cephalosporin compounds which can be applied for the process of this invention include all of the cephalosporin compounds produced by fermentation, for example, cephalosporin C, 7-methoxycephalosporin C, cephamycin C, desacetoxycephalosporin C etc.; semi- or total-synthesized cephalosporin compounds, including all of the pharmaceutically applicable cephalosporin compounds and intermediates for preparation thereof, for example, 7-aminocephalosporanic acid, 7-amino-3-methyl-3-cephem-4-carboxylic acid, 7-amino-7-methoxycephalosporanic acid, 7-amino-3-cephem-4-carboxylic acid, 7-amino-3-carbamoyloxymethyl-3-cephem-4-carboxylic acid, 7-amino-3-hydroxymethyl-3-cephem-4-carboxylic acid, 7-amino-3-heterocyclicthiomethyl-3-cephem-4-carboxylic acid [e.g. 7-amino-3-(5-methyl-1,3,4-thiadiazol-2-ylthiomethyl)-3-cephem-4-carboxylic acid, 7-amino-3-(1-methyl-1H-tetrazol-5-ylthiomethyl)-3-cephem-4-carboxylic acid, 7-amino-3-(1H-1,2,3-triazol-5-ylthiomethyl)-3-cephem-4-carboxylic acid, 7-amino-3-(1,3,4-thiadiazol-2-ylthiomethyl)-3-cephem-4-carboxylic acid] and all the corresponding 7-N-acylated derivatives of the above mentioned 7-amino compounds, etc.; and a salt at the amino and/or carboxy group thereof.

The solution containing the cephalosporin compound for which the process of this invention can be applied include a solution containing the cephalosporin compound stemming from the fermentation broth and/or from the synthesizing process.

As a solution containing cephalosporin compound stemming from the fermentation broth, there are usually used the filtrate of a fermentation broth, the pre-extracted culture solution which can be obtained by pre-extraction of the broth in a conventional manner described in the prior arts as mentioned above and the like.

Further, as a solution containing a semi- or total-synthesized cephalosporin compound, there may be used the reaction mixture per se, a solution which is obtained by preextraction of the reaction mixture in a conventional manner, a solution of the crude product as isolated in a conventional manner, and the like.

The macroporous, non-ionic adsorption resin to be used in the process of this invention may be the same as those described in the above prior arts, and may have an average pore diameter of 4 to 100 nm and a surface from 100 to 1000 $m^2$ per gram.

Preferred examples of such resins may include a macroporous, non-ionic styrene-divinyl benzene copolymer, homopolymer of acrylic ester, sulfoxide or amide, and the like, and more particularly, there may be exemplified Amberlite XAD-1, XAD-2, XAD-4, XAD-7, XAD-8, XAD-9, XAD-11 and XAD-12 (Trademark, manufactured by Rohm and Haas Co.), Diaion HP-10, HP-20, HP-30, HP-40 and HP-50 (Trademark, manufactured by Mitsubishi Chemical Industries Ltd.), Imacti Syn-42, Syn-44 and Syn-46 (Trademark, manufactured by Imacti Co.), and the like.

The treatment of a solution containing the cephalosporin compound in admixture with impurities with the macroporous, non-ionic adsorption resin is conducted substantially in the same manner as described in the prior arts as mentioned above, for instance, by a batch system or column system operation.

The cephalosporin compound adsorbed on the resin is then eluted from the resin with an aqueous solution containing an anionic surface active agent. As preferred examples of the anionic surface active agent, there may be exemplified an alkali metal salt of higher alkyl sulfate (e.g. sodium lauryl sulfate, etc.), alkylbenzenesulfonate, and the like.

The concentration of the anionic surface active agent contained in the aqueous solution for the elution of the adsorbed cephalosporin compound is not restrictive, but the concentration of around 1% (w/v) thereof may be usually sufficient.

In the elution operation, it is noted that washing of the resin with water in advance of the elution may be occasionally preferable to recover the adsorbed cephalosporin compound from the resin in higher purity.

The object cephalosporin compound thus eluted can be recovered in a solid form from the eluate by a conventional manner such as concentration, lyophilization, precipitation, crystallization and the like.

In such case as a slight amount of the anionic surface active agent is contained in the obtained solid substance as an impurity according to a method applied for the recovery, it can be easily removed off from the resultant solid substance by simply washing it with a small amount of alcohol (e.g. ethanol, etc.) or the like.

The resin can be easily regenerated by a conventional manner as described in U.S. Pat. No. 3,725,400, for example, by washing it with a mixture of a 1N-aqueous sodium hydroxide solution and acetone, aqueous acetone or alcohol (e.g. methanol), an aqueous solution of an acid such as oxalic acid, sulfuric acid, hydrochloric acid, or the like.

As illustrated as above, the superior point of this invention to the known processes is that a highly purified cephalosporin compound can be provided effectively by using the specified eluent in the process of the present invention.

The following Examples are given for illustrating the present invention in more detail.

EXAMPLE 1

A filtrate (200 ml.) of fermentation broth containing sodium salt of cephalosporin C (32.73 μ/ml) was passed through a 32 mm diameter column charged with macroporous non-ionic adsorption resin "Diaion HP-20" (Trademark, manufactured by Mitsubishi Chemical Industries Ltd.) (100 ml.) at a flow rate of sv=0.4. The resin in the column was washed with water (100 ml.), and then the sodium salt of cephalosporin C was eluted with a 1% (w/v) aqueous solution of sodium lauryl sulfate (manufactured by Nikko Chemicals Co., Ltd.) at a flow rate of sv=0.4. The eluate (500 ml., containing 93.3% of the initial potency) was concentrated under reduced pressure and treated with ethanol. The resultant precipitates were collected by filtration, washed with 90% ethanol (5 ml.) and then dried to give sodium salt of cephalosporin C, purity of which was determined as 54.8% by liquid chromatography.

EXAMPLE 2

In the same operation as Example 1, a 1% (w/v) aqueous solution of alkyl benzenesulfonate (manufactured by The Lion Fat and Oil Co., Ltd.) was used as an eluent instead of the 1% (w/v) aqueous solution of sodium lauryl sulfate. The eluate (500 ml., containing 91.9% of the initial potency) was treated in the same manner as described in Example 1 to give sodium salt of cephalosporin C, purity of which was determined as 82.4% by liquid chromatography.

EXAMPLE 3

An aqueous reaction mixture (6.76 ml.) containing 7-(5-aminoadipinamido)-3-(5-methyl-1,3,4-thiadiazol-2-ylthiomethyl)-3-cephem-4-carboxylic acid (content: 84.8 mg/ml), which had been prepared by the reaction of sodium salt of cephalosporin C with sodium salt of 5-methyl-1,3,4-thiadiazole-2-thiol, was adjusted to pH 3.2 and passed through a 20 mm diameter column charged with macroporous, non-ionic adsorption resin "Diaion HP-20" (Trademark, manufactured by Mitsubishi Chemical Industries Ltd.) (30 ml.) at a flow rate of sv=0.5. The resin in the column was washed with water (60 ml.), and then the adsorved compound was eluted with a 1% (w/v) aqueous solution of sodium lauryl sulfate (manufactured by Nikko Chemicals Co., Ltd.) at a flow rate of sv=0.5. The eluate (220 ml., containing 64.9% of the theoretical amount) was adjusted to pH 6.8 with an aqueous solution of sodium hydroxide and concentrated under reduced pressure. The residue was treated with acetone, and the precipitates were collected by filtration and dried to give sodium 7-(5-aminoadipinamido)-3-(5-methyl-1,3,4-thiadiazol-2-ylthiomethyl)-3-cephem-4-carboxylate (recovery from the eluate: 96.6%), purity of which was determined as 83.6% by liquid chromatography.

A comparative test was carried out by using 50% isopropyl alcohol as an eluent, which is described in the U.S. Pat. No. 3,725,400, instead of the 1% aqueous solution of sodium lauryl sulfate. The purity of the compound thus obtained was 62.0%.

EXAMPLE 4

An aqueous reaction mixture (6.76 ml.) containing 7-(5-aminoadipinamido)-3-(1,3,4-thiadiazol-2-ylthiomethyl)-3-cephem-4-carboxylic acid (content: 103 mg/ml.), which had been prepared by the reaction of sodium salt of cephalosporin C with sodium salt of 1,3,4-thiadiazole-2-thiol, was adjusted to pH 3.2 and treated in the same manner as described in Example 3. The eluate (222 ml., containing 73.9% of the theoretical amount) was adjusted to pH 6.8 with aqueous ammonium hydroxide and then concentrated under reduced pressure. The residue was treated with acetone, and the resultant precipitates were collected by filtration and dried to give ammonium salt of 7-(5-aminoadipinamido)-3-(1,3,4-thiadiazol-2-ylthiomethyl)-3-cephem-4-carboxylic acid (recovery from the eluate: 83.3%), purity of which was determined as 83.4% by liquid chromatography.

We claim:

1. In the process for the isolation of a cephalosporin compound from a solution thereof in admixture with impurities, by treating the solution with macroporous, non-ionic styrene-divinylbenzene copolymer adsorption resin and then eluting the adsorbed cephalosporin compound from the resin, the improvement of eluting the adsorbed cephalosporin compound from the resin with an aqueous solution of anionic surface active agent selected from alkali metal (higher) alkyl sulfate and alkylbenzenesulfonate.

2. A process according to claim 1, wherein the cephalosporin compound is cephalosporin C.

3. A process according to claim 1, wherein the cephalosporin compound is 7-(5-aminoadipinamido)-3-(5-methyl-1,3,4-thiadiazol-2-ylthiomethyl)-3-cephem-4-carboxylic acid.

4. A process according to claim 1, wherein the cephalosporin compound is 7-(5-aminoadipinamido)-3-(1,3,4-thiadiazol-2-ylthiomethyl)-3-cephem-4-carboxylic acid.

5. A process according to claim 1, wherein the cephalosporin compound is 7-(5-aminoadipinamido)-3-(1- methyl-1H-tetrazol-5-ylthiomethyl)-3-cephem-4-carboxylic acid.

6. A process according to claim 1, wherein the anionic surface active agent is alkali metal lauryl sulfate.

7. A process according to claim 1, wherein the anionic surface active agent is sodium lauryl sulfate.

8. A process according to claim 1, wherein the anionic surface active agent is alkylbenzenesulfonate.

9. A process according to claim 1, wherein the concentration of the anionic surface active agent contained in the aqueous solution is around 1% (w/v).